(12) United States Patent
Nigam et al.

(10) Patent No.: US 6,548,692 B1
(45) Date of Patent: Apr. 15, 2003

(54) METHOD FOR PREPARING 1,2-DIBROMO-2,4-DICYANOBUTANE

(75) Inventors: Satish C. Nigam, Hilliard, OH (US); Cletis Stiffler, Grove City, OH (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/132,022

(22) Filed: Apr. 25, 2002

(51) Int. Cl.⁷ .................. C07C 255/04; C07C 255/06
(52) U.S. Cl. ........................ 558/461; 558/435
(58) Field of Search .............. 424/304; 558/461, 558/435

(56) References Cited

U.S. PATENT DOCUMENTS

| | | | |
|---|---|---|---|
| 3,833,731 A | 9/1974 | Grier et al. ............ 424/304 |
| 3,849,422 A | 11/1974 | Weis ............ 360/290 |
| 3,877,922 A * | 4/1975 | Grier et al. ............ 71/67 |
| 3,929,858 A | 12/1975 | Swigert ............ 260/465.7 |
| 4,504,423 A * | 3/1985 | Higaki et al. ............ 260/465.7 |
| 5,942,240 A | 8/1999 | Merianos et al. ............ 424/405 |

\* cited by examiner

*Primary Examiner*—Joseph K. McKane
*Assistant Examiner*—Rei-Tsang Shiao
(74) *Attorney, Agent, or Firm*—Imre Balogh; William J. Davis

(57) ABSTRACT

Method for preparing 1,2-dibromo-2,4-dicyanobutane by reacting 2-methyleneglutaronitrile with bromine in an alcoholic solvent at a temperature of about 25° C. to 65° C. and isolating the product in one unit operation without color or odor problems and in high yields.

10 Claims, No Drawings

METHOD FOR PREPARING 1,2-DIBROMO-2,4-DICYANOBUTANE

BACKGROUND OF THE INVENTION

1. Field of the Invention

This invention relates to an improved process for the manufacture of 1,2-dibromo-2,4-dicyanobutane.

2. Reported Developments 1,2-dibromo-2,4-dicyanobutane is well known in the prior art and is being sold as MERGUARD® 1200 by Calgon and as INTEGRA® CG-20 by International Specialty Products, Inc. The compound, also known as 2-bromo-2-bromomethylglutaronitrile, exhibits excellent preservative activity in use in compositions of personal care, nutritional and pharmaceutical products. It is produced by several methods, using the technique of bromination of 2-methyleneglutaronitrile, as described, for example, in U.S. Pat. Nos. 3,929,858, 3,877,922, 3,849,422, 3,873,597, 3,833,731 and 3,644,380.

Purification to eliminate coloration and irritating odor is described in U.S. Pat. No. 4,504,423.

Generally characterized, the prior art describes the addition of excess bromine to a suspension of 2-methyleneglutaronitrile at high temperatures. The reaction is completed in about 4 to 8 hours. The excess bromine is decomposed. On cooling, the reaction mixture is solidified, filtered, and washed repeatedly with water and sodium carbonate or a nitrate solution. The product is then recrystallized from an alcohol, such as methanol, and isolated in one or two crops.

Some disadvantages have been observed with the product made by some of the disclosed processes including the following.

In all cases at least 2–3 unit operations are involved; the reaction is heterogeneous; higher operating temperatures are required to complete the reaction in a reasonable time; the process train requires specialized reactors, centrifuges and driers to constrain corrosion; in most cases the upper aqueous layer that is highly acidic needs to be decanted off; which is industrially unfeasible; and the recrystallization process requires, sometimes in two crops, additional equipment and time.

Accordingly, it is an object of the present invention to provide a process to prepare 1,2-dibromo-2,4-dicyanobutane which avoids these and other disadvantages and produces a solid form of the compound free of any color and irritating odor.

SUMMARY OF THE INVENTION

The improved process of the present invention comprises:

mixing 2-methyleneglutaronitrile with a polar, non-aqueous alcoholic solvent selected from the group consisting of methanol, ethanol, and isopropanol to obtain a solution;

gradually adding bromine to the solution and carrying out the reaction at about 25° C. to about 65° C., and preferably at about 30° C.;

neutralizing the solution with a 5% sodium bicarbonate solution to neutral pH;

adding water to the solution while cooling to precipitate;

filtering and washing the product; and drying the product under vacuum at low temperatures.

In reacting 2-methyleneglutaronitrile with bromine, 1 to 2 mole % less of bromine is used to insure that no free bromine is present at the completion of the reaction.

The final product is a white crystalline solid that is free of discoloration and irritating odor even on drying and extended storage.

DETAILED DESCRIPTION OF THE INVENTION

Example 1 further illustrates the process of the present invention.

EXAMPLE 1

The reaction is carried out in a 4 L cylindrical, 4-neck jacketed flask equipped with a cold-water condenser, motor driven paddle stirrer, thermometer, and a dropping funnel. The flask is charged with 800 g of 2-methyleneglutaronitrile and 2.8 L of methanol. Then, 1.2 kg bromine is added gradually over a period of two hours while maintaining the batch temperature below 40° C. After the addition of bromine, the homogeneous reaction mixture is warmed to 50–55° C. for one to two hours. Then 5% sodium bicarbonate is gradually added to neutralize the reaction mixture to a pH of 6–7. After neutralization, additional water is added to saturate the methanolic solution for crystallization. Crystallization starts at about 30° C. The methanolic solution containing the crystals therein are cooled to about 5° C. and filtered to obtain a cake. The cake is then washed with pre-cooled methanol/water mixture and dried in a vacuum oven at 25°–40° C. The colorless shining crystals with no odor had a melting point at 52° C. Yield was 1.84 kg which is 94% of theoretical yield.

The product obtained by the process of the present invention was compared for color in the form of solid and 5% ethanol solution with a commercial product in solid form and in 5% ethanol solution.

The result is shown in Table I.

TABLE I

| Color (APHA) | This Product | Commercial Product |
|---|---|---|
| Solid | <1 | <6 |
| 5% Ethanol solution (after 2 days) | <1 | ~200 Yellow |

EXAMPLE 2

For comparison of color, odor and yield, products produced by method known in the prior art literature were made and tested. The experiments were carried out with and without solvents in two unit operations, namely, reaction followed by recrystallization. In most cases an additional washing and purification was required to bring the products into acceptable limits for color and odor. The results for the product made by the process of the present invention using methanol and the products made by prior art processes are shown in Table II.

TABLE II

| Solvent | Color | Odor | Yield % |
|---|---|---|---|
| Methanol | Colorless | None | 94 |
| Neat | Off-white | Slightly Pungent | 87 |
| Methylene Chloride | Off-white | Slightly Pungent | 88 |
| Water | Off-white | Slightly Pungent | 83.5 |

Changes and modifications may be made to the improved process of the present invention which are within the skill of the art which changes and modifications can be made without departing from the spirit and scope thereof.

What is claimed is:

1. A method for preparing 1,2-dibromo-2,4-dicyanobutane comprising: reacting 2-methyleneglutaronitrile and bromine in an alcoholic solvent at a temperature of about 25° C. to 65° C. to obtain a reaction mixture.

2. The method of claim 1 wherein said alcoholic solvent is selected from the group consisting of methanol, ethanol and isopropanol.

3. The method of claim 1 comprising neutralizing the reaction mixture to pH 6–7.

4. The method of claim 3 wherein said neutralization is with the use of sodium bicarbonate.

5. The method of claim 1 wherein the reaction is carried out in a single container.

6. The method of claim 4 wherein 1,2-dibromo-2,4-dicyanobutane is produced as white crystals without irritating odor.

7. A method for preparing 1,2-dibromo-2,4-dicyanobutane comprising the steps of:

mixing 2-methyleneglutaronitrile with methanol to obtain a solution;

gradually adding bromine to the solution by maintaining the solution temperature below 40° C. to obtain a homogenous reaction mixture;

warming the homogeneous reaction mixture to about 50°–55° C.;

gradually adding a 5% sodium bicarbonate solution to the reaction mixture to neutralize the reaction mixture to a pH of 6–7;

adding water to the reaction mixture to saturate the reaction mixture for crystallization;

cooling the reaction mixture to about 5° C. to obtain the product in the form of a cake;

filtering the cake out of the reaction mixture;

washing the cake with a pre-cooled methanol/water mixture;

drying the cake in a vacuum oven at 25°–40° C. to obtain the 1,2-dibromo-2,4-dicyanobutane as colorless crystals.

8. The method of claim 7 comprising reacting 1 to 2 moles % less bromine that the molar equivalent of bromine to 2-methyleneglutaronitrile.

9. The method of claim 8 wherein 1 to 2 mole % less of bromine is used as compared to the mole % of 2-methyleneglutaronitrile.

10. The method of claim 7 wherein the reaction between bromine and 2-methyleneglutaronitrile is carried out at a temperature of about 30° C.

* * * * *